United States Patent [19]

Coyne et al.

[11] Patent Number: 4,715,217

[45] Date of Patent: Dec. 29, 1987

[54] DETERMINING ORGANIC COMPOUNDS USING A MEMBRANE

[75] Inventors: Brenton S. Coyne; Andrew J. Strandjord; Mark W. Spence; Reid S. Willis; Robert A. Bredeweg; Timothy S. Stevens, all of Midland, Mich.

[73] Assignee: The Dow Chemical Company, Midland, Mich.

[21] Appl. No.: 903,535

[22] Filed: Sep. 4, 1986

Related U.S. Application Data

[63] Continuation-in-part of Ser. No. 742,151, Jun. 6, 1985.

[51] Int. Cl.$^4$ .............................................. B01D 15/08
[52] U.S. Cl. .................................... 73/61.1 C; 73/19; 210/656
[58] Field of Search ..................... 73/61 R, 19, 61.1 C, 73/23.1; 210/321.2, 198.2, 656; 55/158, 67

[56] References Cited

U.S. PATENT DOCUMENTS

| | | | |
|---|---|---|---|
| 3,419,144 | 12/1968 | Huntington | 210/644 |
| 3,438,241 | 4/1969 | McKinley, Jr. | 73/23 |
| 3,850,203 | 11/1974 | Shobert | 138/125 |
| 3,891,556 | 6/1975 | Richardson et al. | 210/490 |
| 3,926,561 | 12/1975 | Lucero | 73/38 |
| 4,022,249 | 5/1977 | de Putter | 138/178 |
| 4,158,629 | 6/1979 | Sawyer | 210/137 |
| 4,239,624 | 12/1980 | van Zon | 210/236 |
| 4,257,257 | 3/1981 | Dairaku et al. | 73/19 |
| 4,378,981 | 4/1983 | Otstot et al. | 55/158 |
| 4,448,691 | 5/1984 | Davis | 210/656 |
| 4,451,374 | 5/1984 | Peterson et al. | 210/198.2 |
| 4,468,948 | 9/1984 | Nakayama | 73/19 |
| 4,529,521 | 7/1985 | Cortes et al. | 210/635 |
| 4,533,518 | 8/1985 | Hanaoka et al. | 210/198.2 |

OTHER PUBLICATIONS

Jennings, Walter, "Gas Chromatography with Glass Capillary Columns," Second Edition, 1980, pp. 81–82.

Primary Examiner—Jerry W. Myracle
Assistant Examiner—Hezron E. Williams
Attorney, Agent, or Firm—Timothy S. Stevens

[57] ABSTRACT

The invention relates to a membrane assisted analytical chemical method for the determination of the concentration of an organic compound in an aqueous matrix. The membrane partitions the matrix from a receiving fluid. The organic compound permeates the membrane and passes into the receiving fluid which is then analyzed for the permeated compound by, for example, liquid or gas chromatography. The membrane is selected to prevent contamination of the receiving fluid from otherwise interfering components of the matrix. The concentration of the organic compound is above its solubility limit in water which would ordinarily prevent effective use of such a membrane assisted method. However, when the organic compound is emulsified with, for example, a surfactant, then a membrane assisted method is successful. The sensitivity of the method can be improved by using a thermal focusing-/gas chromatography technique to concentrate the permeated organic compound from the receiving fluid and the membrane can be protected from physical damage by enclosing it in a perforate structure.

14 Claims, 2 Drawing Figures

DETERMINING ORGANIC COMPOUNDS USING A MEMBRANE

CROSS-REFERENCE TO RELATED APPLICATION

This application is a continuation-in-part of the copending application Ser. No. 742,151, filed June 6, 1985 which is hereby incorporated by reference.

FIELD OF THE INVENTION

The present invention relates to an analytical chemistry method for determining the concentration of an organic compound in an aqueous matrix and where the concentration is above the solubility limit of the compound in water.

BACKGROUND OF THE INVENTION

The analytical chemistry technique comprising partitioning a sample to be analyzed from a preselected receiving fluid with a membrane is known. The membrane is selected to be permeable to the compound in the sample to be analyzed and the compound then passes into the receiving fluid which can be a gas or a liquid. The receiving fluid can then be flowed to, for example, a gas or liquid chromatograph in order to separate and quantify the permeated compound. The membrane is selected to prevent effective contamination of the receiving fluid with other sample components that would otherwise significantly interfere with quantitation.

An example of this type of membrane assisted analytical chemistry is U. S. Pat. No. 4,257,257 to Dairaku et al. wherein the receiving fluid is a gas and the means to quantify the permeated compound is a gas chromatograph. Dairaku et al. discuss the use of both porous and nonporous membranes.

Another example of this type of membrane assisted analytical chemistry is U.S. Pat. No. 4,529,521 to Cortes et al. wherein the receiving fluid is a liquid and the means to quantify the permeated compound is a liquid chromatograph. Cortes et al. discuss the determination of water-soluble monomers in latex products and do not discuss the situation where the monomer concentration is above its solubility limit.

The present inventors were frustrated when they tried to use the above-mentioned inventions for the determination of monomers during polymerization and synthesis of commercial latex products. The problem occurred when the concentration of the monomer exceeded its solubility limit in the aqueous matrix used for latex production. When the solubility limit is exceeded, then droplets of monomer form in the matrix and the calibration curve for analysis, as shown, for example, in FIG. 3 of Dairaku et al., supra, either (a) becomes flat and the method therefore is unusable due to the fact that above the solubility limit the aqueous phase next to the membrane contains a constant concentration of the monomer; or (b) the calibration curve spikes upward unpredictably and thus the method is therefore unusable due to droplets of monomer coating the membrane with a resulting very high permeation of monomer through the membrane.

The present invention solves this problem by effectively emulsifying the droplets of organic compound in the aqueous matrix using, for example, a surfactant. When this is done, then the calibration curve continues to rise predictably and reproducibly and thus usably in the concentration range above the solubility limit in water of the compound to be analyzed.

SUMMARY OF THE INVENTION

The invention is a membrane assisted analytical chemical method for effective determination of the concentration of an emulsified organic compound essentially completely emulsified with an emulsifying agent in an aqueous matrix wherein the concentration is greater than the solubility limit of the compound in water comprising the steps of: (a) partitioning the matrix from a receiving fluid with the membrane which is selected to be permeable to at least a detectable amount of the compound; and (b) determining the concentration of the compound dispersed in the receiving fluid.

When the receiving fluid is a gas, then a gas chromatograph can be used to determine the concentration of the permeated compound in the receiving fluid if the permeated compound is volatile in the receiving fluid. Similarly, when the receiving fluid is a liquid, then a liquid chromatograph can be used to determine the concentration of the permeated compound in the receiving fluid if the permeated compound is soluble in the receiving fluid.

The emulsifying agent can be an anionic, cationic, nonionic, amphoteric, polymeric or fluorocarbon surfactant and the concentration of a surfactant in the invention can be at least above one-half the critical micelle concentration of the surfactant.

The organic compound can be a monomer such as vinylidene chloride, vinyl chloride, methyl acrylate, methyl methacrylate, butyl acrylate, styrene, butadiene and acrylonitrile. The organic compound can also be a hydrocarbon such as naptha, gasoline, kerosene, fuel oil, lubricating oil, grease and chlorinated solvent.

The membrane can be in the form of a tubular membrane such as silicone rubber tubing and can be protected from physical damage by a perforate housing member disposed around the membrane. The membrane can also be in the form of a sheet membrane.

When a gas chromatograph is used to determine the concentration of the permeated compound in the receiving fluid, then a thermal focusing technique can be employed to improve the limit of detection of the permeated compound in the receiving fluid.

DETAILED DESCRIPTION OF THE INVENTION

Figure 1:
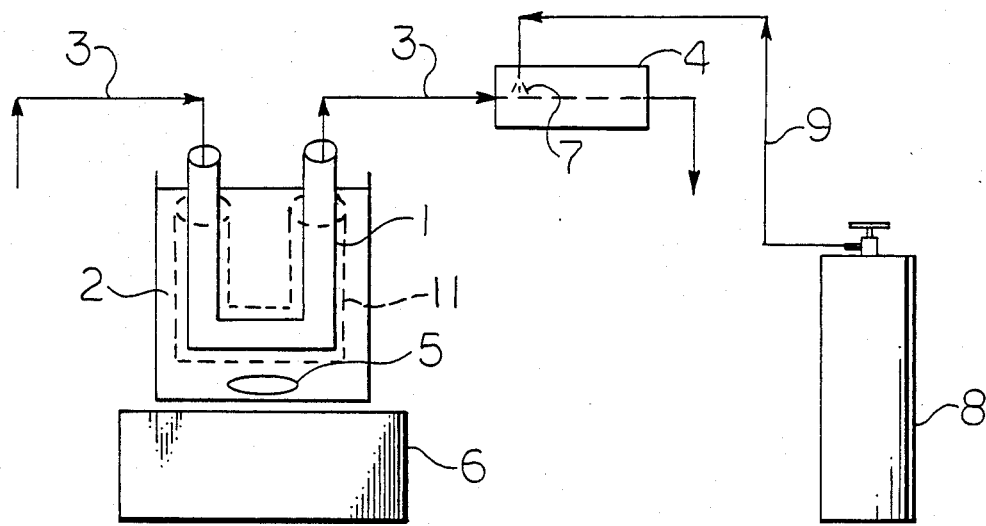
FIG. 1 is a drawing of an apparatus that can be used in practicing the method of the invention using a tubular membrane.

Referring to FIG. 1, therein is shown an apparatus using a tubular membrane 1 that can be used in the method of the invention. The purpose of the invention is to determine the concentration of an emulsified organic compound in an aqueous matrix 2, wherein the concentration of the compound is greater than the solubility limit of the compound in water and the compound is emulsified with an emulsifying agent. The membrane 1 is selected to be permeable to the compound. The membrane 1 partitions the matrix 2 from a flowing stream of receiving fluid 3 and the permeated compound then passes into the fluid 3 which is then directed to an analytical chemical means 4 to determine the concentration of the compound in the fluid 3. The concentration of the compound in the matrix 2 is then calculated from the concentration of the compound in the fluid 3 as determined by the means 4. The system can be calibrated by adding a known amount of the compound to the matrix 2 and then noting the increase in response of means 4 to the compound. In this way a calibration curve can be plotted relating the concentration of the compound in the matrix 2 to the concentration of the compound in the fluid 3 as determined by the means 4.

The calibration curve can be effected by the flow rate of the fluid 3, the temperature of the matrix 2 and the length of time the matrix 2 is exposed to the membrane 1. A slower flow rate of the fluid 3 can result in a higher concentration of the permeated compound in the fluid 3 even though the concentration of the compound in the matrix 2 is constant. At higher temperatures of the matrix 2, then generally the concentration of the compound in the fluid 3 is higher even though the concentration of the compound in the matrix 2 is constant. At a given flow rate of the fluid 3, at a given concentration of the compound in the matrix 2 and at a given matrix 2 temperature, the concentration of the permeated compound in the fluid 3 varies with time. At the time when the matrix 2 is first contacted with the membrane 1, the concentration of the permeated compound in the fluid 3 is zero. Then, this concentration increases until a steady state is reached followed by a generally gradual decrease in this concentration as the matrix 2 is depleted of the compound.

Generally, it is also preferable to stir the matrix 2 for the most consistant and reproducible results and this can be accomplished with, for example, a magnetic stir bar 5 driven by a magnetic stirrer 6. The stirring rate can effect the concentration of the permeated compound in the fluid 3 and at a relatively high stirring rate, the concentration of the compound in the fluid 3 can be increased relative to a slower stirring rate even though the concentration of the compound in the matrix 2 is constant. In addition, the permeation characteristics of the membrane can change with time due to, for example, aging or fouling of the membrane surface from components of the matrix 2.

Therefore, the present invention is preferably calibrated and then an analysis performed under known and controlled conditions of system temperature, flow rate of fluid 3, stirring rate of stir bar 5 and time between initial contact of the matrix 2 with the membrane 1, which is preferably long enough for the concentration of the compound in the fluid 3 to come to a relatively constant value. Additionally, recalibration is preferably performed as needed to compensate for any changes in the permeation characteristics of the membrane, such as membrane fouling.

The receiving fluid 3 can comprise a gas or a liquid. The specific gas or liquid is not critical to the invention as long as the permeated organic compound is either volatile in the gas or soluble in the liquid used. When the receiving fluid 3 is a liquid, then the analytical means 4 can comprise a liquid chromatograph. Some liquid chromatographic systems are slowly poisoned by emulsifying agents and in this event a nonporous membrane is preferred as being less likely to allow permeation of the emulsifying agent across the membrane 1. When using a gas chromatograph as the analytical means 4, then the detection limit of the gas chromatograph to a low concentration of permeated compound in the fluid 3 can be improved by the additional technique of thermal focusing.

As used in the present invention, thermal focusing comprises cooling the fluid 3 to condense and concentrate the permeated compound. Preferably, the thermal focusing is accomplished by spraying liquid carbon dioxide 7 onto the front of the gas chromatographic column contained in means 4 which cools the front of the column to about $-40°$ C. The liquid carbon dioxide ($CO_2$) is preferably obtained from a standard syphon $CO_2$ tank 8 conducted by tubing 9.

Preferably, a perforate housing member 11 is disposed around the membrane 1 to protect the membrane 1 from physical damage, e.g., from the stirring bar 5.

Figure 2:
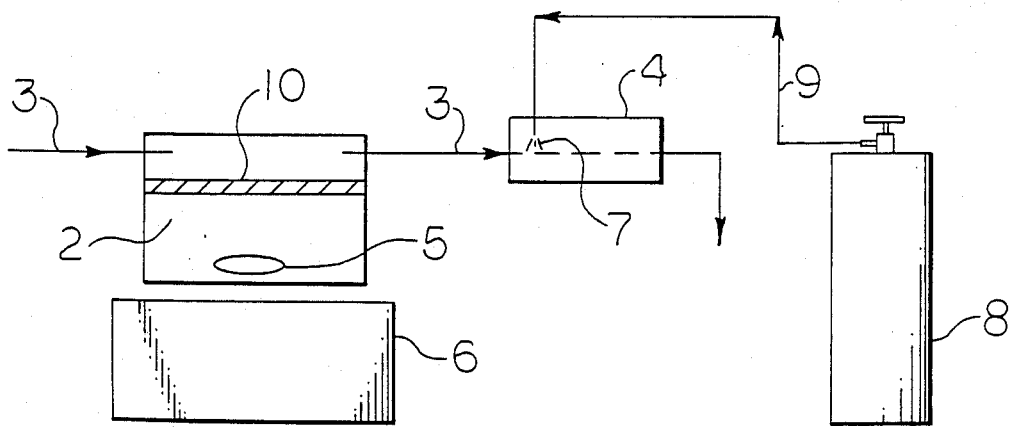
FIG. 2 is a drawing of an apparatus that can be used in practicing the method of the invention using a sheet membrane.

FIG. 2 shows an equivalent apparatus to that of FIG. 1 but with the use of a sheet form membrane 10. Generally, the specific membrane used is not critical as long as it is permeable to the compound. A highly preferred tubular membrane 1 is 0.012 inch I.D., 0.025 inch O.D. Dow Corning Silastic silicone rubber medical tubing. Silicone rubber is permeable to many emulsifiable organic compounds and yet silicone rubber is effectively impermeable to most emulsifying agents and relatively impermeable to water relative to a porous membrane. However, in many cases a porous membrane, such as Celgard tubular membrane or Celgard sheet membrane, available from the Celanese Corporation, is preferred since generally porous membranes have a lower resistance to permeation of emulsifiable organic compounds than nonporous membranes such as silicone rubber. The term "membrane" means one or more tubular membranes or one or more sheet form membranes used to partition the matrix 2 from the receiving fluid 3.

The membrane 1 can be fragile and can be damaged by, for example, becoming tangled in the stirring bar 5. Preferably, the membrane 1 is housed inside a perforated stainless steel tube to protect the membrane from physical damage and yet still allow contact of the membrane 1 with the matrix 2.

The emulsified organic compound in the matrix 2 can be relatively volatile, e.g., styrene or vinylidene chloride or relatively nonvolatile, e.g., no. 2 fuel oil or SAE 30 lubricating oil. In any event, the permeated compound must be soluble or volatile in the fluid 3 in order to effectively utilize the analytical means 4. Generally, a volatile permeated compound can be analyzed by a means 4 comprising a gas chromatograph and a nonvolatile permeated compound can be analyzed by a means 4 comprising a liquid chromatograph.

The term "organic compound" means a single chemical species such as styrene monomer as well as mixtures of chemical species such as styrene and butadiene monomers or more complex mixtures of chemical species such as the hydrocarbon mixture no. 2 fuel oil. When it is desired to quantify individual chemical species, the means 4 generally comprises a chromatograph. However, the means 4 can simply be, for example, a flame ionization detector or a flow through UV spectrophotometer. The specific analytical means 4 is not critical as long as it is capable of effective determination of the permeated compound in the fluid 3.

The specific aqueous matrix 2 is not critical in the invention and comprises ground or surface water contaminated with, for example, gasoline or chlorinated dry cleaning solvent above its solubility limit in water as well as latex products containing, for example, a monomer above the solubility limit of the monomer in water.

The specific emulsifying agent is not critical in the invention as long as it is capable of emulsifying the organic compound and as long as enough of the emulsifying agent is present in the matrix 2 to emulsify the organic compound. Surfactants are preferred emulsifying agents and all forms of surfactants, e.g., ionic, nonionic, anionic and cationic surfactants are believed generally usable. As is well known in the art of emulsifying emulsifiable organic compounds in aqueous matrices, some surfactants work better than others in specific cases. For example, high ionic strength matrices respond well to surfactants like Dowfax 2A-1, available from The Dow Chemical Company. Often several surfactants are blended for optimum emulsification performance and the term "emulsifying agent" herein is meant to include such blends of surfactants. Preferably, the concentration of a surfactant is at least above one-half the critical micelle concentration of the surfactant.

EXAMPLES

The invention is further described in the following examples and comparative examples.

EXAMPLE 1

A system generally similar to FIG. 1 is assembled. The membrane 1 is a bundle of Silastic silicone rubber tubing, supra. Three parallel strands of tubing, each 18 inches long are tube sheeted at each end of the bundle to conventional 1/16×1/16 inch stainless steel tubing unions using Dow Corning RTV silicone rubber bathtub caulk. The receiving fluid 3 is GC grade nitrogen ($N_2$) conducted from a $N_2$ cylinder and regulator to one of the 1/16×1/16 inch stainless steel tube unions by 0.04 inch I.D.×1/16 inch O.D. stainless steel tubing. The flow of $N_2$ then is split into 3 equal streams down the bore of each silicone rubber tube and is then recombined at the other 1/16×1/16 inch stainless steel tube union. The flow of $N_2$ then is conducted by 0.04 inch I.D.×1/16 inch O.D. inch stainless steel tubing to a Valco loop injection valve incorporating a 500 µl injection loop.

The injection valve is mounted in the column oven of a Hewlett Packard (HP) 5710 gas chromatograph (GC) which outputs to a HP 3388 integrator/recorder. The HP 5710 GC incorporates a ⅛ inch×10 foot long column of 10 percent SP-1000 or 80/100 mesh Supelcoport with a carrier flow rate of 30 ml per minute (ml/min) of helium and an oven temperature of 120° C. The HP 5710 GC also incorporates a flame ionization detector operated at 300° C.

The bundle of silicone rubber membranes is immersed in a constantly stirred water solution containing 4 percent Dowfax 2A-1 surfactant, supra. The $N_2$ flow rate is adjusted to be about 30 ml/min. After 10 minutes, the injection valve is rotated to inject 500 µl of $N_2$ onto the column. No response is seen from the GC at the retention time of vinylidene chloride. A 500 µl standard containing 33 µl of vinylidene chloride per 4 l of air is injected onto the column and a vinylidene chloride peak at 0.81 minutes that has an area of 37,457 is reported by the HP 3388.

This example demonstrates an apparatus of the invention using multiple membranes and also includes an example analysis of a blank sample.

EXAMPLE 2

The system of Example 1 is exactly reproduced in this comparative example except that the membranes are immersed in Saran latex containing about 50 percent by weight of a 90:10 vinylidene chloride:methyl methacrylate copolymer as beads about 1,200 Å in diameter and about 50 percent by weight of 0.2 percent Dowfax 2A-1 in water. This concentration is below ½ of the critical micelle concentration of Dowfax 2A-1. To the latex is added 3 weight percent vinylidene chloride monomer which is not emulsified and which is seen to fall to the bottom of the container. After 10 minutes, the injection valve is rotated to inject 500 µl of $N_2$ receiving gas onto the column and a vinylidene chloride peak is observed but its peak area is much lower than it should have been relative to the amount of vinylidene chloride added to the latex. Then, the stirring rate of the magnetic stirrer is increased and droplets of vinylidene chloride are seen to be swept up into the latex and to adhere to the membrane. After 10 minutes, the injection valve is rotated to inject 500 µl of $N_2$ receiving gas into the column and a vinylidene chloride peak is observed but its peak area is much larger than it should have been relative to the amount of vinylidene chloride added to the latex.

EXAMPLE 3

The system of Example 1 is exactly reproduced except that the membranes are immersed in Saran latex containing about 50 percent by weight of a 90:10 vinylidene chloride:methyl methacrylate copolymer as beads about 1,200 Å in diameter and about 50 percent by weight of 4 percent Dowfax 2A-1 in water. This concentration is above ½ of the critical micelle concentration of Dowfax 2A-1. After 10 minutes, the injection valve is rotated to inject 500 µl of $N_2$ receiving gas onto the column and a vinylidene chloride peak is observed having a peak area of 1,050 according to the HP 3388 integrator. Therefore, it is estimated that the vinylidene chloride concentration in the $N_2$ receiver gas is 0.23 mg per liter. Then, the membranes are suspended in additional samples of the same latex composition as above except that vinylidene chloride is spiked into the latex at various concentrations and again analyzed as above. The added vinylidene chloride is emulsified by the surfactant in the latex. Table I shows the resulting data.

TABLE I

VINYLIDENE CHLORIDE CONCENTRATION IN THE SAMPLE MATRIX AND THE RECEIVING GAS FOR THE SYSTEM OF EXAMPLE 3

| Vinylidene Chloride Concentration of the: | |
|---|---|
| Sample[a] | Receiving Gas |
| 400 mg/l | 1.23 mg/l |
| 1,400 mg/l | 4.84 mg/l |
| 3,400 mg/l | 9.02 mg/l |
| 7,400 mg/l | 20.5 mg/l |
| 13,400 mg/l | 37.4 mg/l |
| 21,400 mg/l | 55.2 mg/l |

[a] Not including the vinylidene chloride in the sample originally.

The data in Table I indicate that the response of the GC is proportional to the concentration of vinylidene chloride in the sample matrix even though the concentration of vinylidene chloride in the sample is greater than its solubility limit in water. The data in Table I also allows an estimation of the original concentration of vinylidene chloride in the latex of 92 mg per liter.

This example demonstrates the use of the invention for a single emulsified organic compound to be analyzed.

EXAMPLE 4

The system of Example 3 is exactly reproduced except that the latex is spiked with vinylidene chloride to a concentration of 1,000 mg per liter and methyl methacrylate to a concentration of 100 mg per liter. After 10 minutes, the injection valve is rotated to inject 500 μl of the $N_2$ receiving gas onto the column. Two peaks are observed on the resulting chromatogram shown by the HP 3388 integrator/recorder, one for vinylidene chloride having an area of 18,800 and one for methyl methacrylate having an area of 1,400. Then, more methyl methacrylate is added to the latex to a total added concentration of 200 mg per liter and 10 minutes later the injection valve is again rotated and an analysis performed as above which results in a vinylidene chloride peak area of 19,800 and a methyl methacrylate peak area of 3,180.

This example demonstrates the use of the invention for a mixture of emulsified organic compounds to be analyzed.

EXAMPLE 5

A 4 inch long section of 0.04 inch I.D.×1/16 inch O.D. length of stainless steel tubing is connected at each end to Valco 1/16 stainless steel tees (catalog no. H 4058, Anspec Inc., Ann Arbor, Mich.). A 1 inch long section of 0.04 inch I.D.×1/16 inch O.D. length of stainless steel tubing is then attached to each tee so that all 3 sections of tubing connected to the 2 tees form a straight line. A 10 inch long section of Silastic membrane, supra, is then inserted through the bore of the 3 sections of tubing with excess membrane extending from the end of each 1 inch section of 1/16 inch stainless steel tubing. Duro 2-ton epoxy resin is then injected into the space between the outside of the Silastic membrane and the inside of the 1 inch sections of 1/16 inch stainless steel tubing. After the epoxy resin has cured, the Silastic membrane is cut flush with the ends of the stainless steel tubing with a razor blade.

A 500 μl sample of Saran latex is injected into a flowing stream of water containing 1 percent sodium lauryl sulfate at a flow rate of 1 ml/min. The stream is then passed through a 5×100 mm liquid chromatography column (Anspec catalog no. H 5884) packed with 3 mm diameter glass beads which mixes the injected latex with the aqueous carrier. The stream is then directed down the bore of the membrane device, above, and then to waste. Helium at a flow rate of 30 ml/min is inputted to the remaining port of one of the stainless steel tees of the membrane device and thus flows around the outside of the membrane and then out the remaining port of the other stainless steel tee of the membrane device to a ⅛ inch×3 foot long gas chromatographic column packed with 80-100 mesh Tenax (available from Anspec Inc.). The column is placed in a Varian 3700 gas chromatograph which outputs to a Spectra Physics 4270 integrator/recorder.

Liquid $CO_2$ from a syphon tank is directed through an on/off valve to the front of the GC column in such a manner that the front of the column is sprayed with liquid $CO_2$ and thus is cooled to about −40° C.

Emulsified organic components in the injected latex sample permeate the membrane and are swept by the helium stream to the front of the GC column where they condense (are thermally focused). Eight minutes after injecting the latex, the flow of liquid $CO_2$ is shut off and the helium flow from the membrane device is vented to the atmosphere. A different helium stream is then directed through the column at a flow rate of 30 ml/min. The column front of the GC column warms up to the temperature of the GC oven (100° C.) and the flow of the helium through the column causes the condensed organic components to volatilize and differentially migrate through the column to the GC detector. The resulting chromatogram shows a vinylidene chloride peak. A calibration curve is prepared by injecting latex containing known concentrations of vinylidene chloride by the procedure above and noting the resulting peak area. The calibration curve is linear in the range from less than 50 ppm to greater than 3,000 ppm vinylidene chloride in the latex.

This example demonstrates the use of thermal focusing in the invention and the exposure of the membrane to the sample matrix in an intermittant and easily automated manner that nevertheless maintains the sensitivity of analysis of the invention.

EXAMPLE 6

The system and procedure of Example 5 is exactly reproduced with the following exceptions. The stream of helium receiving gas is directed down the bore of a 4 inch long length of Silastic membrane, supra, inserted inside a 4 inch long section of centrally slotted 0.04 inch I.D.×1/16 inch O.D. stainless steel tubing. Duro 2-ton epoxy resin is used as in Example 5 to seal the Silastic membrane to the ends of the stainless steel tubing. The center 40 mm section of the stainless steel tubing was slotted by partially cutting through the tubing with an SSI tubing cutter (Anspec catalog no. A 3475). Twenty slots were cut to thus expose and yet protect the membrane from physical damage (such as a magnetic stirring bar spinning out of control). The stainless steel tube is then bent in a U form, with the slotted section at the bottom of the U, and immersed in a stirred sample of latex diluted 1:20 with 1 percent sodium lauryl sulfate in water. A calibration curve is prepared by immersing the protected membrane into the diluted latex solutions containing known concentrations of vinylidene chloride and noting the resulting peak area. The calibration curve is linear from less than 70 ppm to greater than 1,000 ppm vinylidene chloride in the original undiluted latex.

This example is an additional example of use of thermal focusing in the invention with the use of a membrane covered by a perforate structure to protect the membrane from physical damage.

Wrapping the membrane around an inert rod immersed in the sample matrix is another effective means of preventing a stirring bar from becoming tangled in the membrane.

EXAMPLE 7

The system of Example 1 is exactly reproduced except that the injection loop is changed to a 120 μl size, the flow rate of $N_2$ receiving gas is changed to 28 ml/min, the GC column is changed to an 8 foot×150 inch stainless steel Varian 1,400 G P/W 20 percent Carbowax 20 M on 60/80 CP-AW and the GC integrator/recorder is changed to a HP Model 3380-A.

The bundle of silicone rubber membranes is immersed in a constantly stirred solution of 430 ml of 3 percent Dowfax 2A-1 in water to which is added 50 μl of hexane. The hexane is seen to be emulsified by the Dowfax 2A-1 surfactant. After 20 minutes, the injection valve is rotated to inject 120 μl of $N_2$ receiving gas onto the column and a hexane peak is observed having a peak area reported by the GC integrator of 177,400 units. Then, the above solution is replaced with an identical solution except that 100 μl of hexane is added to the solution. The hexane is seen to be emulsified by the Dowfax 2A-1 surfactant. After 20 minutes, the injection valve is again rotated and a hexane peak having an area of 363,000 units is observed.

The data in this example indicate that the response of the GC is proportional to the concentration of hexane over the range studied when the hexane is emulsified in the aqueous sample matrix even though the concentration range of hexane studied is greater than its solubility limit in water.

This example demonstrates the use of the invention for the determination of organic solvents.

What is claimed is:

1. In a membrane assisted analytical chemical method for the determination of the concentration of an organic compound in an aqueous matrix wherein said concentration is greater than the solubility limit of said compound in water, comprising the steps of:
   (a) adding an emulsifying agent to said matrix to essentially completely emulsify said organic compound;
   (b) partitioning said matrix from a receiving fluid with said membrane, said membrane permeable to at least a detectable amount of said compound; and
   (c) determining the concentration of said compound dispersed in said receiving fluid.

2. The method of claim 1 wherein said receiving fluid is a gas, wherein a gas chromatograph is used for said step of determining the concentration of said compound in said receiving fluid and wherein said compound is volatile in said receiving fluid.

3. The method of claim 1 wherein said receiving fluid is a liquid, wherein liquid chromatography is used for said step of determining the concentration of said compound in said receiving fluid and wherein said compound is soluble in said receiving fluid.

4. The method of claim 1 wherein said emulsifying agent is selected from the group consisting of anionic, cationic, nonionic, amphoteric, polymeric and fluorocarbon surfactants.

5. The method of claim 4 wherein the concentration of said surfactant is at least above one-half the critical micelle concentration of said surfactant.

6. The method of claim 1 wherein said compound is a monomer.

7. The improved method of claim 6 wherein said monomer is selected from the group consisting of vinylidene chloride, vinyl chloride, methyl acrylate, methyl methacrylate, butyl acrylate, styrene, butadiene, and acrylonitrile.

8. The method of claim 1 wherein said compound is a hydrocarbon.

9. The method of claim 8 wherein said hydrocarbon is selected from the group consisting of naptha, gasoline, kerosene, fuel oil, lubricating oil, grease and chlorinated solvent.

10. The method of claim 1 wherein said membrane is in the form of a tubular membrane.

11. The method of claim 10 wherein said membrane is protected from physical damage by a perforate housing member disposed around said membrane.

12. The method of claim 10 wherein said membrane comprises silicone rubber.

13. The method of claim 1 wherein said membrane is in the form of a sheet membrane.

14. The method of claim 2 further comprising the step of thermally focusing said compound from said receiving fluid in order to improve the limit of detection of said step of determining the concentration of said compound in said receiving fluid by said gas chromatograph.

* * * * *

UNITED STATES PATENT AND TRADEMARK OFFICE
CERTIFICATE OF CORRECTION

PATENT NO. : 4,715,217

DATED : December 29, 1987

INVENTOR(S) : Brenton S. Coyne; Andrew J. Strandjord; Mark W. Spence; Reid S. Willis; Robert A. Bredeweg; Timothy S. Stevens It is certified that error appears in the above-identified patent and that said Letters Patent is hereby corrected as shown below:

Col. 5, line 39, delete the second occurrence of "inch" (between "O.D." and stainless").

Col. 8, line 56, "reproduoed" should read -- reproduced --;
　　　　line 59, "150" should read -- 1/8 --.

Signed and Sealed this

Seventeenth Day of October, 1989

Attest:

DONALD J. QUIGG

Attesting Officer

Commissioner of Patents and Trademarks